United States Patent
Lueder et al.

[11] Patent Number: 6,140,302
[45] Date of Patent: Oct. 31, 2000

[54] METHOD FOR PRODUCING ANIONIC SURFACTANT GRANULATES

[75] Inventors: Thomas Lueder, Langenfeld; Bernhard Gutsche, Hilden; Konstantinos Scholinakis, Monheim, all of Germany

[73] Assignee: Cognis Deutschland GmbH, Duesseldorf, Germany

[21] Appl. No.: 09/380,917

[22] PCT Filed: Mar. 3, 1998

[86] PCT No.: PCT/EP98/01173

§ 371 Date: Oct. 29, 1999

§ 102(e) Date: Oct. 29, 1999

[87] PCT Pub. No.: WO98/40461

PCT Pub. Date: Sep. 17, 1998

[30] Foreign Application Priority Data

Mar. 12, 1997 [DE] Germany .................... 197 10 152

[51] Int. Cl.⁷ .................................................. C11D 11/00
[52] U.S. Cl. .................... 510/444; 510/446; 510/457; 510/458; 510/495; 510/535; 510/536; 23/313 FB; 159/48.1; 562/45; 562/97
[58] Field of Search .................. 510/444, 446, 510/457, 458, 495, 535, 536; 23/313 FB; 159/48.1; 562/45, 97

[56] References Cited

U.S. PATENT DOCUMENTS 5,189,207 2/1993 Blasey et al. ................. 562/97

FOREIGN PATENT DOCUMENTS

| 0 345 090 | 6/1989 | European Pat. Off. . |
| 0 402 112 | 12/1989 | European Pat. Off. . |
| 37 41 401 | 6/1989 | Germany . |
| WO96/06917 | 12/1990 | WIPO . |
| WO96/06916 | 3/1996 | WIPO . |

OTHER PUBLICATIONS

Surfactants in Consumer Products (1987) pp. 54–127.
Katalysatoren, Tenside and Mineraloeladditive (1978) pp. 123–217.

*Primary Examiner*—Necholus Ogden
*Attorney, Agent, or Firm*—John E. Drach; Henry E. Millson, Jr.

[57] ABSTRACT

A process for the production of anionic surfactant granules comprising the steps of:

A) Neutralizing an acidic anionic surfactant with a base in a horizontal thin-layer evaporator or thin-layer dryer; and B) Drying the resulting neutralized anionic surfactant in the evaporator or dryer to form surfactant granules; wherein the acidic anionic surfactant and the base taken together have a solids content such that the total quantity of water in the evaporator or dryer at no time exceeds about 15 % by weight and wherein the neutralization and drying are carried out in countercurrent flow with air or an alkaline gas stream at a temperature in the range of from about 120 to about 130° C.

26 Claims, No Drawings

METHOD FOR PRODUCING ANIONIC SURFACTANT GRANULATES

FIELD OF THE INVENTION

This invention relates to an improved process for the production of anionic surfactant granules in which water-containing anionic surfactant pastes in their acidic form are subjected at a defined solids content to simultaneous neutralization, drying and granulation in a thin-layer evaporator or dryer.

1. Prior Art

Anionic surfactants are normally produced in several process steps. The sulfonation step is followed by neutralization with lyes in an aqueous medium and, finally, the water is removed to the required content in a concluding drying step. The production costs are determined to a very large extent by the quantity of water which ultimately has to be removed from the product. It will readily be appreciated that every effort should be made to keep this quantity as small as possible and, if possible, to eliminate the need for the drying step altogether.

Accordingly, various attempts have been made in the past to provide such processes and to improve process economy by reducing the energy costs and increasing the throughput. However, reducing the water content in the neutralization step leads through gel formation to a steep increase in the viscosity of the products which is accompanied by inhomogeneities in the product through inadequate mixing of the acidic anionic surfactant and the base used for neutralization. Accordingly, highly concentrated anionic surfactant pastes with residual water contents of at least 25 to 35% by weight can still just be produced and dried in correspondingly adapted industrial installations.

Another approach based on a different concept is to integrate neutralization and drying into a single process step. German patent application DE-A1 3741401 (Henkel) describes a process in which aqueous acidic anionic surfactants and aqueous neutralization bases are exposed to a gas stream and then dried by spraying. International patent application WO 96/06917 (Unilever) describes a process for the production of anionic surfactant granules in which water-containing, acidic anionic surfactants are mixed with water-containing neutralizing agents in a horizontally arranged thin-layer evaporator or dryer, so that neutralized preparations with a water content above 20% by weight are formed and are subsequently dried at temperatures above 130° C. to the required water content of less than 20% by weight and, at the same time, granulated. The high water content in the neutralization step is unfavorable from the energy point of view and, in addition, leads to a comparatively low throughput. Balancing of the described neutralization of aqueous alkyl sulfuric acid semiester with 30% by weight sodium hydroxide shows that a product with a total water content of at least 25% by weight is formed in the meantime and is then dried.

By contrast, International patent application WO 96/06916 (Unilever) describes a process for drying water-containing anionic surfactant pastes in a horizontal thin-layer evaporator which is carried out at temperatures above 130° C. under a light vacuum to almost normal pressure. Another feature of this process is the use of a very high peripheral speed of the stirrers used of at least 15 m/s which virtually rules out direct wall contact and leads to light-colored products. However, in the drying of water-containing anionic surfactant pastes, more particularly water-containing pastes of alkyl sulfates or alkyl ether sulfates, there is basically a danger of unwanted hydrolysis in the product. Even a brief local reduction in the pH value leads in the presence of water to re-hydrolysis, to the formation of inorganic sulfate and to a reduction in the content of washing-active substance. In following the teaching of WO 96/06916, applicants found that a hydrolysis-free product could not be reproducibly obtained over an operating period of several hours.

Accordingly, the problem addressed by the present invention was to provide a process for the production of anionic surfactant granules by simultaneous neutralization, drying and granulation which would not have any of the disadvantages described above.

2. Description of the Invention

The present invention relates to a process for the production of anionic surfactant granules by simultaneous neutralization of acidic anionic surfactants with bases, drying and granulation in a thin-layer evaporator or dryer, characterized in that the acidic anionic surfactants and/or the bases are used in the form of aqueous preparations with such a solids content that the total quantity of water in the installation at no time exceeds 15% by weight.

It has surprisingly been found that simultaneous drying and neutralization in a thin-layer dryer can be carried out with excellent results even when the dryer is directly charged with water-free or highly concentrated, water-containing acidic anionic surfactants and highly concentrated water-containing bases so that, over the process as a whole, i.e. during neutralization, drying and granulation, the total water content does not exceed 15% by weight, preferably 10% by weight. Compared with the process according to WO 96/06917, the total water balance was reduced by up to 44% and the throughput improved by more than 60%. In addition, the throughput can be further increased by partly recycling dry product. In one particularly preferred embodiment, the neutralization/drying step is carried out at 120 to 130° C. which leads to particularly free-flowing granules of satisfactory color.

Acidic Anionic Surfactants

Typical examples of anionic surfactants which may be produced using the process according to the invention are soaps, alkyl benzenesulfonates, alkane sulfonates, olefin sulfonates, alkyl ether sulfonates, glycerol ether sulfonates, α-methyl ester sulfonates, sulfofatty acids, alkyl sulfates, fatty alcohol ether sulfates, glycerol ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids such as, for example, acyl lactylates, acyl tartrates, acyl glutamates and acyl aspartates, alkyl oligoglucoside sulfates, protein fatty acid condensates (more particularly vegetable wheat-based products), alkyl (ether) phosphates and sulfates of ring-opening products of olefin epoxides with water or alcohols. Where the anionic surfactants contain polyglycol ether chains, they may have a conventional homolog distribution although they preferably have a narrow homolog distribution. The surfactants mentioned are all known compounds. Information on the structure and production of these substances can be found in relevant synoptic works, cf. for example J. Falbe (ed.), "Surfactants in Consumer Products", Springer Verlag, Berlin, 1987, pages 54–124 or J. Falbe (ed.), "Katalysatoren, Tenside und Mineralöladditive", Thieme Verlag, Stuttgart, 1978, pages 123–217. Before drying, the surfactants are present in their acidic, i.e. non-neutralized form, and may be used either as aqueous preparations with a solids content of 80 to 99.9% by weight and preferably 85 to 95% by weight or as water-free preparations. Carboxylic acids, sulfuric acid semiesters of alcohols or alcohol ethoxylates and alkyl benzenesulfonic acids, which give soaps, alkyl (ether) sulfates or alkyl benzenesulfonates after neutralization, are preferably used.

Carboxylic Acids

Carboxylic acids which, after neutralization, give soaps and which may be used as starting materials for the process according to the invention correspond to formula (I):

$$R^1CO\text{—}OH \qquad (I)$$

in which $R^1CO$ is a linear or branched alkyl and/or alkenyl radical containing 6 to 22 carbon atoms. Typical examples are caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid, erucic acid, Guerbet acids and the technical mixtures thereof which are formed, for example, in the pressure hydrolysis of natural fats and oils, in the reduction of aldehydes from Roelen's oxosynthesis or in the dimerization of unsaturated fatty acids. Technical fatty acids containing 12 to 18 carbon atoms, for example cocofatty acid, palm oil fatty acid, palm kernel oil fatty acid or tallow fatty acid, are preferred.

Alkyl and/or Alkenyl Sulfuric Acid Semiesters

Alkyl and/or alkenyl sulfuric acid semiesters, from which alkyl and/or alkenyl sulfates are formed after neutralization, are the sulfation products of primary alcohols corresponding to formula (II):

$$R^2O\text{—}SO_3H \qquad (II)$$

in which $R^2$ is a linear or branched, aliphatic alkyl and/or alkenyl group containing 6 to 22 and preferably 12 to 18 carbon atoms. Typical examples of sulfuric acid semiesters, which may be used as raw materials in accordance with the present invention, are the sulfation products of caproic alcohol, caprylic alcohol, capric alcohol, 2-ethylhexyl alcohol, lauryl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol and erucyl alcohol and the technical mixtures thereof obtained by high-pressure hydrogenation of technical methyl ester fractions or aldehydes from Roelen's oxosynthesis. Guerbet alcohols containing 16 to 32 carbon atoms may also be used as raw materials. Alkyl sulfuric acid semiesters based on lauryl alcohol, stearyl alcohol and corresponding cocofatty alcohols are particularly preferred.

Sulfuric Acid Semiesters of Alkyl and/or Alkenyl Ethers

The sulfuric acid semiesters of alkyl and/or alkenyl ethers are understood to be acidic anionic surfactants which are industrially produced by sulfation of oxoalcohol or fatty alcohol polyglycol ethers with $SO_3$ or chlorosulfonic acid (CSA) and subsequent neutralization and then give alkyl and/or alkenyl ether sulfates. According to the invention, suitable starting materials for the drying step are sulfuric acid semiesters corresponding to formula (III):

$$R^3O\text{—}(CH_2CH_2O)_mSO_3H \qquad (III)$$

in which $R^3$ is a linear or branched alkyl and/or alkenyl group containing 6 to 22 carbon atoms and m is a number of 1 to 10. Typical examples are the sulfates of products of the addition of, on average, 1 to 10 and, more particularly, 2 to 5 moles of ethylene oxide onto caproic alcohol, caprylic alcohol, 2-ethylhexyl alcohol, capric alcohol, lauryl alcohol, isotridecyl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol and brassidyl alcohol and technical mixtures thereof. Products of the addition of ethylene oxide onto Guerbet alcohols containing 16 to 32 carbon atoms may also be used as raw materials. The sulfation products may have a conventional homolog distribution and a narrow homolog distribution. The use of sulfuric acid semiesters based on adducts of, on average, 2 to 3 moles of ethylene oxide with technical $C_{12/14}$ or $C_{12/18}$ cocofatty alcohol fractions is particularly preferred.

Alkyl Benzenesulfonic Acids

Alkyl benzenesulfonic acids which give alkyl benzenesulfonates after drying are sulfonation products of alkyl benzenes which correspond to formula (IV):

$$R^4\text{—}Ph\text{—}SO_3H \qquad (IV)$$

where $R^4$ is an alkyl group containing 8 to 18 carbon atoms and Ph is a phenyl group. Typical examples of alkyl benzenesulfonic acids are dodecyl and tetradecyl benzenesulfonic acid.

Bases

Whereas the acidic anionic surfactants—viscosity permitting—are used either in water-free form or with only a small quantity of water, the neutralizing agents are always used in the form of highly concentrated aqueous preparations. Such preparations are understood to be solutions of alkali metal and/or alkaline earth metal hydroxides, carbonates and/or hydrogen carbonates such as, for example, sodium hydroxide, sodium carbonate, sodium hydrogen carbonate, potassium hydroxide, potassium carbonate, potassium hydrogen carbonate or ammonia which have a non-aqueous component of at least 35% by weight which is limited solely by the maximum solubility. Accordingly, it is preferred to use about 50 to 55% by weight aqueous solutions of sodium hydroxide or sodium carbonate.

Neutralization, Drying and Granulation in a Thin-Layer Evaporator The simultaneous neutralization, drying and granulation process takes place in a horizontally arranged thin-layer evaporator with rotating internals of the type marketed, for example, by the VRV company under the name of "Flash Dryer" or by the Vomm company under the name of "Turbo Dryer". In simple terms, the flash dryer is a tube which can be heated to different temperatures over several zones. The mixture of acidic anionic surfactant and neutralization base, which is introduced by a pump, is projected onto the heated wall by one or more shafts fitted with paddles or plowshares as rotating internals and is dried on the heated wall in a thin layer typically with the thickness of 1 to 10 mm. In one particular embodiment of the invention, the acidic anionic surfactant and the neutralization base are separately introduced so that mixing takes place in the thin-layer evaporator/dryer. According to the invention, it has been found to be of advantage to apply a temperature gradient of 120–170° C. and preferably 120 to 130° C. (product entrance) to 20° C. (product exit) to the thin layer evaporator. To this end, the first two zones of the evaporator for example may be heated to 120–170° C. and preferably to 120–130° C. and the last zone to 20° C. Higher drying temperatures, although possible, have not been found to be of advantage in view of the thermal lability of the starting materials. A low operating temperature is desirable with the hydrolysis-sensitive sulfuric acid semiester in mind.

The thin-layer evaporator is operated at atmospheric pressure. Air or, for example, an alkaline gas stream (for example air:ammonia=1:1) is passed through in countercurrent (throughput about 50–150 m³/h). The gas entry temperature is generally in the range from 20 to 30° C. while the exit temperature is in the range from 90 to 110° C.

In addition, after drying, it has proved to be of considerable advantage to transfer the granules, which still have a temperature of around 50 to 70° C., to a conveyor belt, preferably in the form of a vibrating shaft, and rapidly to cool them thereon, i.e. over a period of 20 to 60 seconds, to temperatures of around 30 to 40° C. using ambient air. In order further to improve their resistance to the unwanted absorption of water, the granules of surfactants particularly sensitive to hydrolysis may also be "dusted", for example by addition of 0.5 to 2% by weight of silica.

Commercial Applications

The granules obtainable by the process according to the invention may be mixed with other ingredients of powder-form surface-active compositions, for example tower powders for detergents, either in the evaporator/dryer after the neutralization zone or in a subsequent step. The powders may also be readily incorporated in water-based preparations. In fact, no differences in performance properties are observed where the powders are used as opposed to the aqueous starting pastes. The granules may also be incorporated in syndet soap formulations or toothpastes, for example together with fatty acids, fatty acid salts, starch, polyglycol and the like.

EXAMPLES

Example 1

The granules were produced in a Flash Dryer of the type manufactured by VRV S.p.A., Milan, Italy. This is a horizontally arranged thin-layer dryer (length 1100 mm, internal diameter 155 mm) with four shafts and 22 paddles of which the distance from the wall is 2 mm. The dryer had three separate heating and cooling zones and a total heat exchange area of, in all, 0.44 m². The dryer was operated at normal pressure. Water-free dodecyl benzenesulfonic acid heated to 50° C. and 50% by weight aqueous sodium hydroxide solution were separately pumped into the thin-layer dryer by two vibrating pumps at a throughput of 11.5 kg/h. The micromixing of the components required for the complete mixing of the spontaneous reaction was guaranteed by the high-speed rotor (peripheral speed 25/s) within the Flash Dryer. Heating zones 1 and 2 of the thin-layer dryer had been adjusted to 170° C. while its cooling zone 3 had been adjusted to 20° C. Air was passed through the Flash Dryer at a rate of around 110 m³/h. The gas exit temperature was around 65° C. The predried granules which still had a temperature of around 60° C. were transferred to a vibrating chute (length 1 m), exposed to ambient air and cooled to around 40° C. in 30 s. The granules were then dusted with around 1% by weight of silica powder (Sipernat® 50 S). The granules finally obtained were dry and pure white and flowed freely without forming lumps, even after prolonged storage in air. After incorporation in detergent formulations, their behabior was no different from that of a comparison produced by spray drying The characteristic data of the granules are set out in Table 1:

Example 2

A tallow fatty acid containing oleic acid (Edenor® PK 1805) was used in the procedure described in Example 1. The results are set out in Table 1.

TABLE 1

Characteristic data of the Flash Dryer granules

| Characteristic data | 1 | 2 |
|---|---|---|
| Washing-active substance [% by weight] | 95.8 | 95.6 |
| Unsulfated or free fatty acid [% by weight] | 1.4 | 1.4 |
| Sodium hydroxide [% by weight] | 1.0 | 0.9 |
| Sodium sulfate [% by weight] | 1.6 | 1.7 |
| Water [% by weight] | 0.2 | 0.4 |
| Bulk density [g/l] | 566 | 577 |
| Particle size distribution [% by weight] | | |
| <0.1 mm | 0 | 0 |
| >0.1 mm | 0.1 | 0.1 |
| >0.2 mm | 0.4 | 0.7 |
| >0.4 mm | 8.9 | 9.1 |
| >0.8 mm | 52.0 | 46.7 |
| >1.6 mm | 37.5 | 42.1 |
| >3.2 mm | 1.1 | 1.3 |

What is claimed is:

1. In a process for the production of anionic surfactant granules by the neutralization of an acidic anionic surfactant with a base, drying and granulating the dried neutralized anionic surfactant, the improvement wherein
   A) the neutralization, drying and granulation are simultaneously carried out in a horizontal thin-layer evaporator or thin-layer dryer;
   B) the acidic anionic surfactant and the base taken together have a solids content such that the total quantity of water in the evaporator or dryer at no time exceeds about 15% by weight; and
   C) the neutralization and drying step is carried out in countercurrent flow with air or an alkaline gas stream at a temperature in the range of from about 120 to 130° C.

2. The process of claim 1 wherein the acidic anionic surfactant is at least one surfactant selected from the group consisting of carboxylic acids, sulfuric acid semiesters of alcohols or alcohol ethoxylates, and alkyl benzenesulfonic acids.

3. The process of claim 1 wherein the acidic anionic surfactant is used in water-free form.

4. The process of claim 1 wherein the base is an aqueous solution of an alkali metal and/or an alkaline earth metal hydroxide, carbonate, hydrogen carbonate, or ammonia with a non-aqueous component of at least 35% by weight.

5. The process of claim 1 wherein the process is carried out at atmospheric pressure.

6. The process of claim 1 wherein the total quantity of water in the evaporator or dryer does not exceed about 10% by weight.

7. The process of claim 1 wherein the neutralized anionic surfactant produced by the process is selected from the group consisting of soaps, alkyl benzenesulfonates, alkane sulfonates, olefin sulfonates, alkyl ether sulfonates, glycerol ether sulfonates, α-methyl ester sulfonates, sulfofatty acids, alkyl sulfates, fatty alcohol ether sulfates, glycerol ether sulfates, hydroxy mixed ether sulfates, monglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acid salts, fatty acid isethionates, fatty acid sarcosinates, fatty acid taurides, N-acylamino acid salts, acyl tartrates, acyl glutamates, acyl aspartates, alkly oligoglucoside sulfates, protein fatty acid condensates, alkyl (ether) phosphates, and sulfates of ring-opening products of olefin epoxides with water or alcohols.

8. The process of claim 1 wherein the acidic anionic surfactant is present as an aqueous composition having a solids content of from about 80 to about 99.9% by weight.

9. The process of claim 8 wherein said solids content is from about 85 to about 95% by weight.

10. The process of claim 4 wherein the base is an aqueous solution of sodium hydroxide or sodium carbonate containing from about 50 to about 55% by weight of solids.

11. The process of claim 1 wherein the thin-layer evaporator has rotating interval components.

12. The process of claim 1 wherein the acidic anionic surfactant and the base are separately introduced into the thin-layer evaporator or dryer so that mixing takes place therein.

13. The process of claim 1 wherein the alkaline gas stream is comprised of ammonia and air.

14. A process for the production of anionic surfactant granules comprising the steps of:
- A) neutralizing an acidic anionic surfactant with a base in a horizontal thin-layer evaporator or thin-layer dryer; and
- B) drying the resulting neutralized anionic surfactant in the evaporator or dryer to form surfactant granules; wherein the acidic anionic surfactant and the base taken together have a solids content such that the total quantity of water in the evaporator or dryer at no time exceeds about 15% by weight, and wherein the neutralization and drying are carried out in countercurrent flow with air or an alkaline gas stream at a temperature in the range of from about 120 to about 130° C.

15. The process of claim 14 wherein the acidic anionic surfactant is at least one surfactant selected from the group consisting of carboxylic acids, sulfuric acid semiesters of alcohols or alcohol ethoxylates, and alkyl benzenesulfonic acids.

16. The process of claim 14 wherein the acidic anionic surfactant is used in water-free form.

17. The process of claim 14 wherein the base is an aqueous solution of an alkali metal and/or an alkaline earth metal hydroxide, carbonate, hydrogen carbonate, or ammonia with a non-aqueous component of at least 35% by weight.

18. The process of claim 14 wherein the process is carried out at atmospheric pressure.

19. The process of claim 14 wherein the total quantity of water in the evaporator or dryer does not exceed about 10% by weight.

20. The process of claim 14 wherein the acidic anionic surfactant is present as an aqueous composition having a solids content of from about 80 to about 99.9% by weight.

21. The process of claim 20 wherein said solids content is from about 85 to about 95% by weight.

22. The process of claim 14 wherein the neutralized anionic surfactant produced by the process is selected from the group consisting of soaps, alkyl benzenesulfonates, alkane sulfonates, olefin sulfonates, alkyl ether sulfonates, glycerol ether sulfonates, $\alpha$-methyl ester sulfonates, sulfofatty acids, alkyl sulfates, fatty alcohol ether sulfates, glycerol ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acid salts, fatty acid isethionates, fatty acid sarcosinates, fatty acid taurides, N-acylamino acid salts, acyl tartrates, acyl glutamates, acyl aspartates, alkyl oligoglucoside sulfates, protein fatty acid condensates, alkyl (ether) phosphates, and sulfates of ring-opening products of olefin epoxides with water or alcohols.

23. The process of claim 17 wherein the base is an aqueous solution of sodium hydroxide or sodium carbonate containing from about 50 to about 55% by weight of solids.

24. The process of claim 14 wherein the thin-layer evaporator has rotating interval components.

25. The process of claim 14 wherein the acidic anionic surfactant and the base are separately introduced into the thin-layer evaporator or dryer so that mixing takes place therein.

26. The process of claim 14 wherein the alkaline gas stream is comprised of ammonia and air.

* * * * *